(12) United States Patent
Choncholas et al.

(10) Patent No.: US 8,312,879 B2
(45) Date of Patent: Nov. 20, 2012

(54) METHOD AND APPARATUS FOR AIRWAY COMPENSATION CONTROL

(75) Inventors: Gary J. Choncholas, Madison, WI (US); Ronald L. Tobia, Sun Prairie, WI (US)

(73) Assignee: General Electric Company, Schenectady, NY (US)

( * ) Notice: Subject to any disclaimer, the term of this patent is extended or adjusted under 35 U.S.C. 154(b) by 1384 days.

(21) Appl. No.: 11/549,754

(22) Filed: Oct. 16, 2006

(65) Prior Publication Data

US 2011/0087123 A9 Apr. 14, 2011

(51) Int. Cl.
*A61M 16/00* (2006.01)
*A62B 7/00* (2006.01)
(52) U.S. Cl. .......... 128/204.23; 128/204.18; 128/204.21
(58) Field of Classification Search ............. 128/204.18, 128/204.21, 204.23, 204.26–204.28
See application file for complete search history.

(56) References Cited

U.S. PATENT DOCUMENTS

| | | | |
|---|---|---|---|
| 5,088,332 A | | 2/1992 | Merilainen et al. |
| 5,546,935 A | * | 8/1996 | Champeau ............... 128/205.23 |
| 5,555,880 A | * | 9/1996 | Winter et al. ............ 128/204.21 |
| 5,906,204 A | * | 5/1999 | Beran et al. ............. 128/207.14 |
| 6,068,602 A | * | 5/2000 | Tham et al. .................... 600/533 |
| 6,315,739 B1 | * | 11/2001 | Merilainen et al. .......... 600/587 |
| 6,390,092 B1 | * | 5/2002 | Leenhoven ............... 128/204.23 |
| 7,051,736 B2 | * | 5/2006 | Banner et al. ............. 128/204.21 |
| 2002/0104537 A1 | * | 8/2002 | Banner et al. ............. 128/204.25 |
| 2003/0106030 A1 | * | 6/2003 | Keller et al. ...................... 716/4 |
| 2003/0159695 A1 | * | 8/2003 | Younes .................... 128/204.18 |
| 2005/0271660 A1 | * | 12/2005 | Wang ......................... 424/144.1 |
| 2006/0251711 A1 | * | 11/2006 | Konduri et al. ............... 424/450 |

FOREIGN PATENT DOCUMENTS

WO 0232488 A2 4/2002

OTHER PUBLICATIONS

"Apparatus and Method for Identifying FRC and PEEP Characteristics", Choncholas et al., pending U.S. Appl. No. 11/438,244, filed May 22, 2006.
"Automatic Tube Compensation", Drager Medical AG & Co., http://www.draeger-medical.com/MT/internet/EN/us/prodserv/products/ventilation/cc/evitaXL_impact/ventilation_therapy/pd31_evitaxl.jsp, 2006.
"Automatic compensation of endotracheal tube resistance in spontaneously breathing patients", Fabry et al., Technology and Health Care, 1 (1994) 281-291.
"The Dynostatic Algorithm in Adult and Paediatric Respiratory Monitoring", Sondergaard, Institute of Surgical Sciences, p. 66-67.

(Continued)

*Primary Examiner* — Justine Yu
*Assistant Examiner* — Valerie L Skorupa
(74) *Attorney, Agent, or Firm* — Andrus, Sceales, Starke & Sawall, LLP

(57) ABSTRACT

A method for controlling a mechanical ventilator that is supplying medical gas to a patient via an endotracheal tube. A pressure is measured from a patient end of an endotracheal tube. The pressure at the patient end of the endotracheal tube is used to create an improved endotracheal tube resistance model such that the medical gas supplied by the mechanical ventilator may be compensated for the resistance of the endotracheal tube thereby providing increased control over the medical gas that is delivered to the patient's lungs. Additionally, if an obstruction in the patient's airway is detected, the location of the obstruction may be targeted such that the proper remedial treatment or procedure is selected by a clinician.

13 Claims, 4 Drawing Sheets

OTHER PUBLICATIONS

"Spirodynamics", Karason, Institute of Surgical Sciences, Second edition, 2000, pp. 173-179.

"Endotracheal tubes and imposed work of breathing: what should we do about it, if anything", Branson et al., Crit Care 2003.

"Good short-term agreement between measured and calculated tracheal pressure", Lichtwarch-Aschoff et al., British Journal of Anaesthesia, 91 (2): 239-48, 2003.

"Change in Expiratory Flow Detects Partial Endotracheal Tube Obstruction in Pressure-Controlled Ventilation", Kawati et al., Critical Care and Trauma, International Anesthesia Research Society, vol. 103, No. 3, Sep. 2006, pp. 650-657.

"Peak Airway Pressure Increase Is a Late Warning Sign of Partial Endotracheal Tube Obstruction Whereas Change in Expiratory Flow Is an Early Warning Sign", Kawati et al., International Anesthesia Research Society, 2005, pp. 889-893.

* cited by examiner

METHOD AND APPARATUS FOR AIRWAY COMPENSATION CONTROL

FIELD OF THE INVENTION

The present invention relates to the field of mechanical ventilation for providing respiratory support to a patient. More specifically, the present invention relates to a method for determining the resistance of a patient connection and compensating the delivery of gases by the mechanical ventilator based upon the measured resistance.

BACKGROUND OF THE INVENTION

Patients that have respiratory difficulties often must be placed on a mechanical ventilator. These difficulties may be pathological in nature or may be due to the fact that the patient is too weak or sedated to independently perform respiration functions. A breath of medical gas is provided by the mechanical ventilator to the patient via a patient connection under a pressure that is sufficient to overcome the resistance of the patient's airway to fill the lungs. When the pressure of the medical gas is reduced, the natural compliance of the patient's lungs and chest wall forces the delivered breath out of the patient in an expiratory phase.

The patient connection facilitates the delivery of the medical gases from the ventilator where the gases are pressurized to the patient in a manner that directs the gases into the patient's lungs. Patient connections may come in a variety of forms, each with its own advantages and limitations. Ventilation masks are the most simple to attach to the patient; however, these masks tend to form an incomplete pneumatic seal with the patient's airway. A nasal cannula is advantageous when it is desirable that the patient's mouth remain obstruction-free. When a patient is not spontaneously breathing, an endotracheal tube (ETT) is commonly used as the patient connection.

Endotracheal tubes are typically used as a patient connection for a mechanical ventilator with patients that are either unconscious and/or heavily sedated. The endotracheal tube is typically made of plastic and inserted through the patient's mouth and into the trachea such that medical gases from the ventilator are delivered to the patient at a point proximal to the lungs. This method, while invasive, provides a pneumatically sealed connection with the patient that provides improved efficiency in the delivery of medical gases. Often, because of the invasive nature of the intubation process, endotracheal tubes are often used with patients that have longer-term respiratory support needs.

While the use of an endotracheal tube allows for the very careful management of patient respiration, there are limitations associated with the use of endotracheal tubes that are counterproductive to the careful management of patient respiration. Specifically, the buildup of mucus within the endotracheal tube affects the fluid mechanics of the medical gas being delivered to the patient through the endotracheal tube. Since patients receiving an endotracheal tube are on the endotracheal tube for a longer term, mucus from the lungs can build up within the endotracheal tube. Mucus buildup restricts the flow of medical gas through the endotracheal tube such that the patient does not receive the projected flow of medical gas from static mechanical ventilator settings. Currently, there is no method or system for providing an indication of whether there is mucus buildup in the endotracheal tube. Total change in patient airway resistance, as measured at the mouth of the patient, can be monitored but there is no indication whether this increase in airway resistance is due to an obstruction in the endotracheal tube or in the patient's lungs. An indication of where the airway is obstructed is desirable to clinicians because clinicians must direct the clinical remedies for clearing an obstruction to the specific location where the obstruction is located, either the endotracheal tube or the patient's lungs.

As the medical gas flows through the endotracheal tube, fluid mechanics states that the resistance of the endotracheal tube will change as the flow varies between laminar and turbulent flow. However, the type of flow is difficult to directly monitor. Therefore, it is desirable to use measured values to calculate the endotracheal tube resistance.

Furthermore, each element in the breathing circuit of the mechanical ventilator system has resistive properties. Since the resistance of the endotracheal tube is artificial, it is desirable to limit or eliminate the effect of the tube's resistance on the delivery of breaths to a patient. This can be accomplished using the airway resistance compensation (ARC) feature that is typically incorporated on modern ventilators. ARC compensates the pressure waveform so that the patient receives the desired pressure waveform at the patient end of the endotracheal tube. However, the current models for the resistive properties of the endotracheal tube are basic models, typically a fixed transfer function that assumes that the endotracheal tube is of a fixed length and a fixed diameter. Typically, the clinician enters the diameter of the tube and the length is assumed. Although the current model utilizes the length and diameter of the endotracheal tube, many clinicians modify the length of the endotracheal tube during use. Further, the buildup of mucus within the endotracheal tube reduces the effective diameter of the tube. This limits the accuracy of the airway resistance compensation for the resistance since for laminar flow the resistance is related to the fourth power of the diameter of the endotracheal tube, thus filtering the signals the patient actually receives. Specifically, the current models of endotracheal tube resistance do not account for the common practice of a clinician cutting the tube to a shorter length to secure a proper fit within the trachea of the patient or for changes in the endotracheal tube resistance resulting from the buildup of mucus within the endotracheal tube.

Therefore, it is desirable to provide a method of accurately measuring the resistive properties of an endotracheal tube being used to deliver medical gas to the lungs of a patient. It is further desirable that mucus buildup within the endotracheal tube may be detected, such that the mechanical ventilator may compensate for the buildup and/or perform a clearing procedure such that the mucus is removed. Still further, it is desirable to use the measurement of the resistive properties of the endotracheal tube to accurately compensate the pressure and flow of the medical gas delivered by the mechanical ventilator such that the patient receives the desired amount of medical gas during mechanical ventilation.

SUMMARY OF THE INVENTION

An embodiment of the present invention comprises an endotracheal tube that is disposed for insertion through the mouth of a patient and into the trachea of the patient. A tracheal pressure catheter is inserted through the patient's mouth so that one end of the catheter is disposed proximately to the end of the endotracheal tube inserted into the patient such that a measurement of pressure may be obtained from the patient end of the endotracheal tube. In a further embodiment of the present invention, the catheter is inserted into the endotracheal tube such that at least a portion of the catheter is within the endotracheal tube.

In an embodiment of the present invention, a pressure detected at a location between the endotracheal tube and the mechanical ventilator is compared to the pressure detected by the pressure transducer disposed in the endotracheal tube such that a measurement of endotracheal tube resistance may be obtained.

In a still further embodiment of the present invention, the endotracheal tube resistance is monitored such that a change in resistance is indicative of an obstruction within the endotracheal tube.

In a still further embodiment of the present invention, the resistive properties of the endotracheal tube are used by the controls of the mechanical ventilator such that the controls of the mechanical ventilator compensate the pressure and flow of medical gas produced by the mechanical ventilator so that the patient receives the desired amount and pressure of medical gas.

Further features of the method of the present invention will be apparent from the following detailed description, taken in conjunction with the associated drawings.

BRIEF DESCRIPTION OF THE DRAWINGS

The drawings illustrate the best mode contemplated of carrying out the invention. In the drawings.

DETAILED DESCRIPTION OF THE INVENTION

Figure 1:
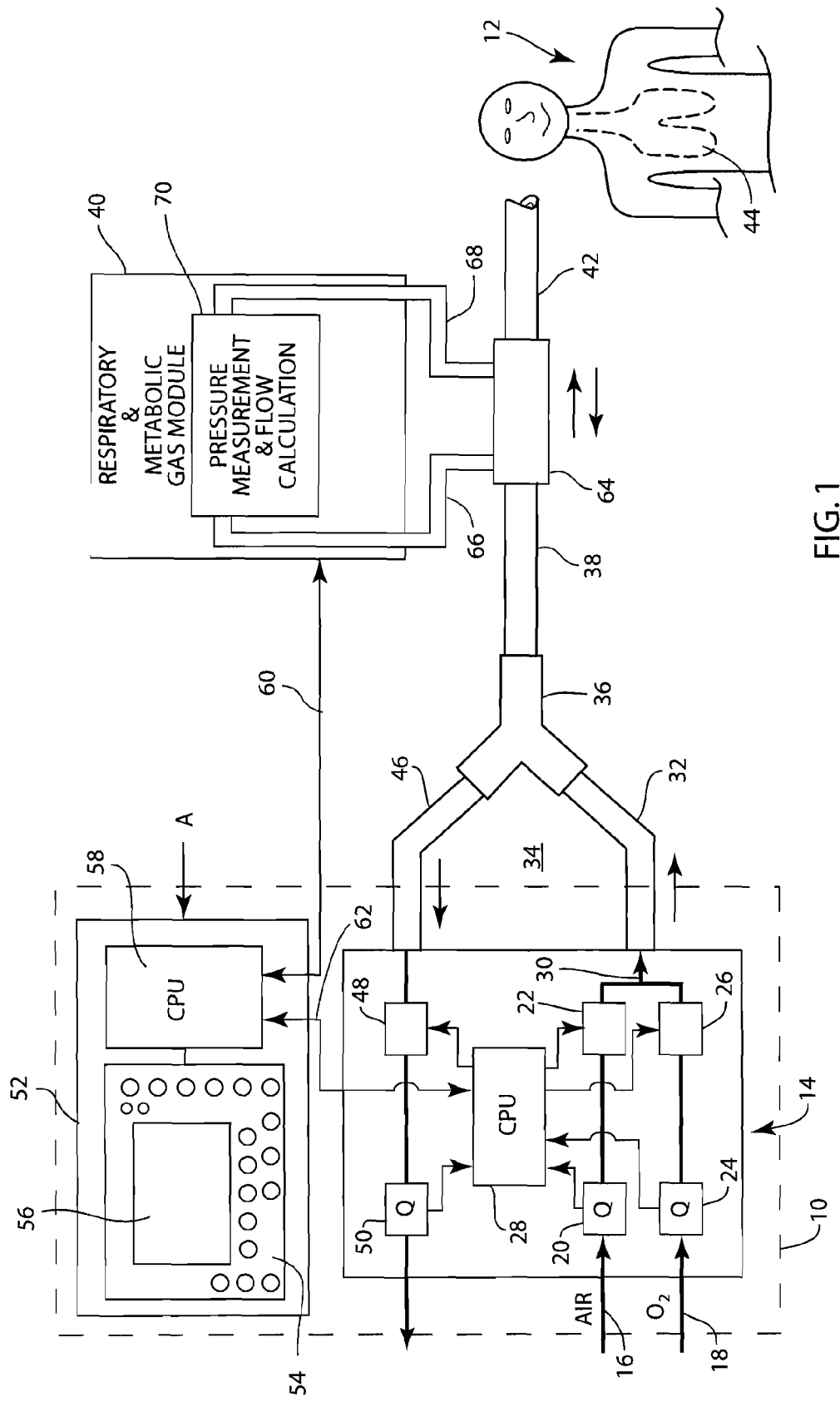
FIG. 1 is a schematic diagram of a mechanical ventilator and the associated apparatus for ventilating a patient.

FIG. 1 depicts a schematic diagram of a mechanical ventilator system 10 set up according to an embodiment of the present invention to provide respiratory support to a patient 12. A ventilator system 10 comprises a mechanical ventilator 14 that performs the mechanical and pneumatic functions of the ventilator system 10 for providing respiratory support to the patient 12. The mechanical ventilator 14 receives medical gas in the form of air 16 but may also receive a supplemental gas such as oxygen 18. The air that is supplied to the patient 12 is regulated by a flow sensor 20 and a control valve 22. Similarly, the supplemental gas 18 is controlled by flow sensor 24 and control valve 26. A controller 28, which may comprise a microprocessor or a CPU, receives flow rates measured by the flow sensors 20 and 24 and controls the amounts of the medical gases 16 and 18 to be delivered to the patient 12 by regulating the control valves 22 and 26.

The term medical gas is used to refer to any gas or combination of gases delivered to a patient in a clinical setting. Thus, whether the patient is receiving ventilatory support with air 16 or with a combination of air 16 and supplemental gas 18 the patient is still receiving medical gas.

The air 16 and any supplemental gas 18 are combined in conduit 30 before entering the inspiratory limb 32 of the breathing circuit 34. The inspiratory limb 32 connects to a Y connector 36 which directs the inspiratory gases into the patient limb 38. The patient limb 38 may comprise a variety of additional respiratory support modules such as a metabolic gas (MGAS) module 40. The medical gas flows through the patient limb to the patient connection 42. The patient connection 42 interacts with the patient 12 such that the medical gas from the mechanical ventilator 14 is directed into the lungs 44 of the patient 12.

When the ventilator 14 has delivered the requisite amount of medical gas to the patient 12, the ventilator 14 cycles to the expiratory phase wherein it stops supplying gas pressure to the lungs 44 of the patient 12. Exhalation commences as the patient's lungs and chest wall force the air out of the patient and back through the patient connection 42 and through the patient limb 38 to the Y connector 36 where it is directed into the expiratory limb 46 of the breathing circuit 34. The expiratory limb 46 delivers the expired air back to the mechanical ventilator 14 where the flow of the expired gas is controlled by control valve 48 and monitored by flow sensor 50 before it is released to the ambient air.

The ventilator system 10 further comprises a ventilator control unit 52. The purpose of the ventilator control unit 52 is to facilitate the interaction between the clinician and the mechanical ventilator 14. The ventilator control unit 52 comprises a user interface 54, which in an embodiment of the invention comprises a plurality of buttons or knobs for the input of information by the clinician. The ventilator control unit 52 further comprises a display 56 where ventilator and patient data or other information is displayed to the clinician. When a clinician enters information into the ventilator control unit 52 via the user interface 54, these signals are processed by a CPU 58. The CPU 58 operates the controls of the user interface 54, but also receives data from other parts of the ventilator including the MGAS module 40. The CPU 58 receives data from the MGAS module 40 via a serial data bus 60. The CPU 58 uses collected data as well as data input by the clinician to send control signals to the controller 28 of the mechanical ventilator 14 via line 62.

The MGAS module 40 comprises a flow restrictor 64 disposed along the patient limb 38. In an embodiment of the present invention, the flow restrictor 64 is located proximally to the patient connection 42. In a still further embodiment (not depicted), flow restrictor 64 is integral with the patient connection 42. The position of the flow restriction 64 proximal to the patient connection 42 results in the pressure detected at the flow restrictor 64 and the flow rate calculated therefrom being indicative of the pressure and flow at the patient connection 42. A first pressure port 66 and a second pressure port 68 are disposed on either side of the flow restrictor 64. The first pressure port 66 and the second pressure port 68 are connected to a pressure measurement component 70 of the MGAS module 40. The pressure measurements and the flow values calculated therefrom are sent back to the CPU 58 via the serial data bus 60.

Figure 2:
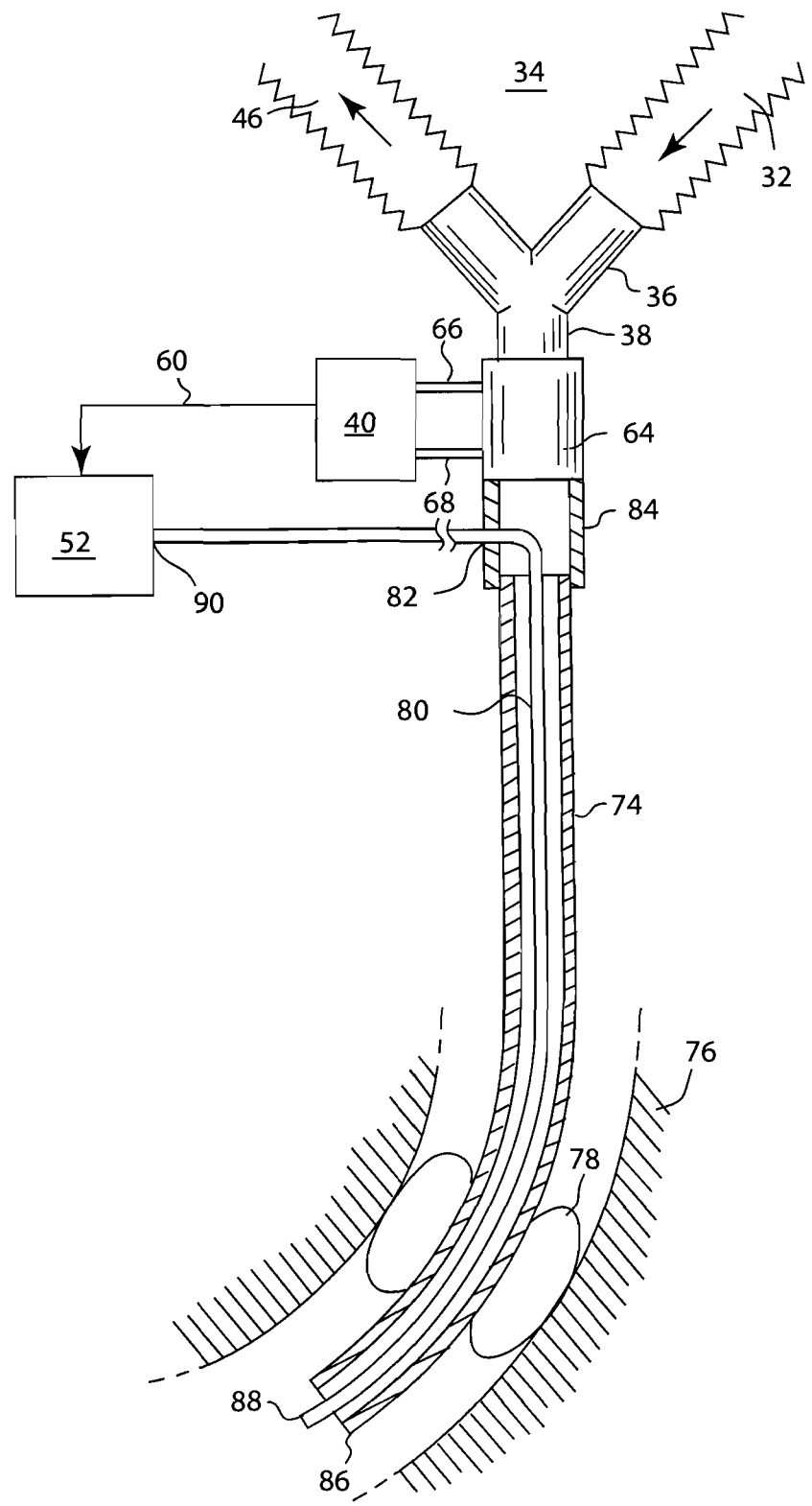
FIG. 2 depicts an endotracheal tube with a tracheal pressure sensor suitable for use with the present invention.

FIG. 2 illustrates an endotracheal tube 74 with a tracheal pressure catheter 80 suitable for use in the present invention. Such an endotracheal tube is disclosed in U.S. Pat. No. 6,315,739 to Merilainen et al, which is hereby incorporated by reference. In the present invention, the patient connection utilized is an endotracheal tube 74. The endotracheal tube 74 is inserted through the mouth of the patient and into the patient's trachea 76 to provide an airway passage to the lungs 44. Once the endotracheal tube 74 is in place, an inflatable cuff 78 that is disposed around the endotracheal tube is inflated such that the endotracheal tube is held into place within the patient's trachea 76.

The endotracheal tube 74 includes a tracheal pressure catheter 80 that is inserted into an opening at point 82 into the endotracheal tube 74. In embodiments of the present invention, the point 82 that the tracheal pressure catheter 80 is inserted into the endotracheal tube 74 may be any point along the endotracheal tube between the ventilator end 84 of the endotracheal tube 74 and the patient end 86 of the endotracheal tube 74. In the embodiment depicted, the point 82 at which the tracheal pressure catheter 80 is inserted into the endotracheal tube 74 is a point that is proximal to the ventilator end 84 of the endotracheal tube 74.

The tracheal pressure catheter 80, after it has been inserted into the endotracheal tube 74 at point 82, extends down the length of the endotracheal tube to the patient end 86. The tracheal pressure catheter 80 terminates at a location proximal to the patient end 86, such that the pressure at the tip 88 of the tracheal pressure catheter 80 is representative of the pressure at the patient end 86. This pressure is representative of the pressure experienced at the approximate end of the endotracheal tube 74 but above the remainder of the patient's bronchial tree and lungs 44.

As illustrated in the embodiment of the invention shown in FIG. 2, the end 90 of the tracheal pressure catheter 80 opposite the tip 88 extends to the control unit 52 and is received at an auxiliary input (Paux). In the embodiment shown in FIG. 2, the control unit includes a pressure transducer (not depicted) that can measure the pressure at the tip 88 of the tracheal pressure catheter 80. Alternatively, it is contemplated that the end 90 of the tracheal pressure catheter 80 could extend to the MGAS module 40. In such an embodiment, the MGAS module 40 comprises an additional pressure transducer (not depicted) such that the pressure at the tip 88 of the tracheal pressure catheter 80 could be measured directly by the MGAS module 40. The pressure measured by the MGAS module 40 could then be relayed to the ventilator control unit 52 by the serial data bus 60. In both described embodiments, a pressure transducer determines the pressure at the tip 88 of the tracheal pressure catheter 80 and this information is utilized by the ventilator control unit 52.

Figure 3:
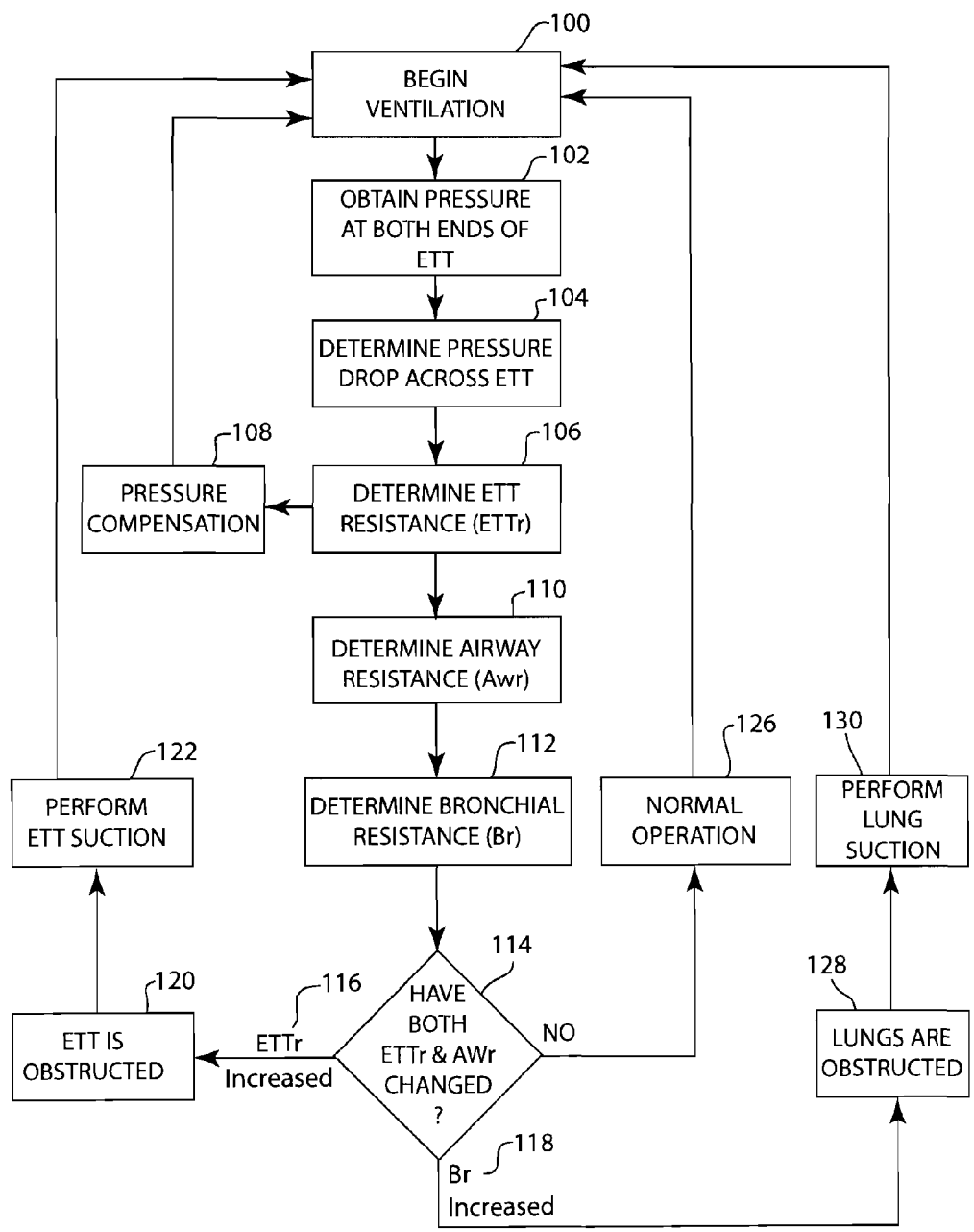
FIG. 3 depicts a flow chart of an embodiment of the method of the present invention.

FIG. 3 is a flow chart that depicts the method of the present invention in reference to the embodiment of the ventilator system 10 previously described in FIGS. 1 and 2. Initially, the clinician begins mechanical ventilation of the patient 12 in step 100. Next, a measurement of the pressure at both ends of the endotracheal tube (ETT) is taken at step 102. In embodiments of the present invention, the pressure at the ventilator end 84 of the endotracheal tube 74, which may be designated the airway pressure (Paw), may be obtained from the ventilator measurements, or may be measured by the pressure sensor 70 of the MGAS module 40. Furthermore, an embodiment of the present invention may connect the end 90 of the tracheal pressure catheter 80 to the control unit 52 where a pressure sensor can determine the pressure at the tip 88 of the tracheal pressure catheter 80. The pressure at the tip 88, which may be designated as the auxiliary pressure (Paux), corresponds to the pressure at the patient end 86 of the endotracheal tube 74. Alternatively, the end 90 of the tracheal pressure catheter 80 may be connected to the MGAS module 40 where a pressure sensor associated with the MGAS module 40 can measure the pressure at the tip 88. In an alternative embodiment, a pressure sensor (not depicted) could be disposed at the tip 88, and an electrical connection (not depicted) could send the sensed pressure back to the CPU 58. Regardless of where the pressure sensors that measure the pressure at either end of the endotracheal tube 74 are, these signals are sent to the CPU 58 of the ventilator control unit 52.

In step 104, the CPU 58 determines the pressure drop ($\Delta P$) across the endotracheal tube 74 by subtracting the airway pressure (Paw) from the auxiliary pressure (Paux). The equation for determining $\Delta P$ is:

$$\Delta P = \text{Paw} - \text{Paux}$$

Next, in step 106, the endotracheal tube resistance (ETTr) is determined. ETTr may be determined by dividing the pressure drop ($\Delta P$) across the endotracheal tube 74 by the flow rate (Q) through the endotracheal tube 74. The equation for this calculation is:

$$\text{ETTr} = \Delta P/Q$$

The flow rate (Q) through the endotracheal tube 74 may be obtained from either the ventilation measurements 14, or may be measured by the MGAS module 40. Additionally, ETTr may be calculated as an instantaneous resistance by dividing any data point value of $\Delta P$ by the corresponding (time dependent) data point value of Q. This may be continuously performed to monitor any changes to ETTr in real-time.

So far, the value of ETTr has been described assuming laminar flow; however, the value of ETTr may change depending on the type of flow of medical gas experienced within the endotracheal tube 74. In turbulent flow, the equation for ETTr changes to $$ETTr = \frac{\Delta P}{Q^2}$$

and when the flow is in transition between laminar and turbulent flow, the equation for ETTr is:

$$ETTr = \frac{\Delta P}{Q^{(1<\alpha<2)}}.$$

This non-linear model of ETTr is made more accurate in the present invention by the use of the measured values of Paw, Paux, and Q, rather than relying on a table of ETTr values based on endotracheal tube diameter as in the prior art. The determination of ETTr may further be extended to include trending and prediction of future ETTr values.

Figure 4:
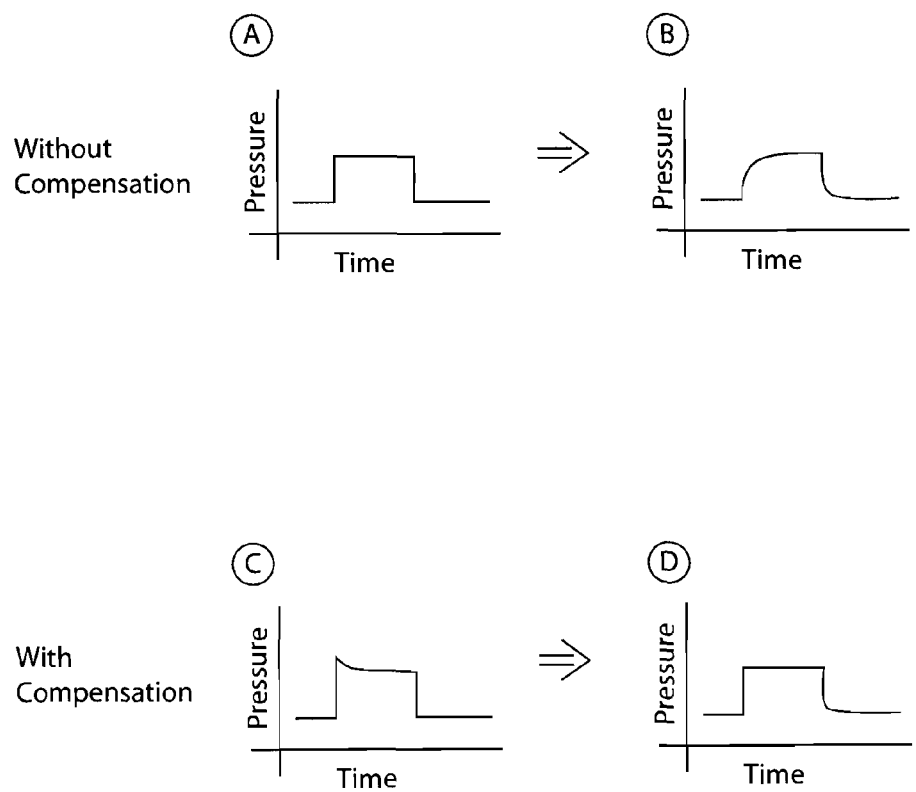
FIG. 4 depicts a series of graphs depicting idealized pressure waveforms supplied by a ventilator and the pressure waveforms received by the lungs of the patient with and without airway compensation.

ETTr may then be used, in step 108, to provide pressure compensation by modifying the pressure of medical gas delivered by the mechanical ventilator to compensate for the resistance of the endotracheal tube. Once the value of ETTr has been determined, the CPU 58 can operate the ventilator to better regulate the pressure of the medical gas at the patient end 86 of the endotracheal tube rather than simply operating to control the pressure delivered at the ventilator end 84 using an apriori resistance model. The ability to monitor the pressure at the endotracheal end allows the ventilator to provide better control of the inspiratory pressure delivered to the patient. Referring to FIG. 4, the initial pressure loss seen in Paux in graph B due to ETTr may be compensated for by initially supplying an amplified pressure for the pressure (Paw) from the ventilator 14 as depicted in graph C. The resulting value of Paux, as depicted in graph D, more closely resembles the desired pressure (Paw) originally provided by the ventilator as depicted in graph A. Since the system allows for the continuous monitoring of the ETTr, the ventilator control unit 52 can continuously modify the pressure delivered by the ventilator to provide the desired pressure waveform to the patient. The pressure compensation of step 108 may be performed on a breath-by-breath basis, continually adjusting for the changing value of ETTr. Furthermore, it may be desirable to filter the ETTr model in the time domain to enhance the model by removing signal noise and outlier data values. For ease of explanation, the pressure waveforms depicted in FIG. 4 are generalized waveforms. It is understood that in actual practice the pressure waveforms observed within the ventilator system will exhibit the general characteristics of the waveforms depicted in FIG. 4.

In an embodiment of the present invention, after the value for the endotracheal tube resistance has been determined in step 106, a determination of the patient's airway resistance (AWr) is made at step 110. The airway resistance may be determined by the CPU 58 by dividing the airway pressure (Paw) by the flow rate (Q) through the endotracheal tube 74. The equation for determining Awr is: Awr=Paw/Q.

Next, at step 112, the patient's bronchial resistance (Br) is determined. In intubated patients, the airway resistance (Awr) comprises the resistance of the patient's bronchial tree, or bronchial resistance (Br), and the resistance of the endotracheal tube (ETTr). Therefore, bronchial resistance (Br) is determined by subtracting endotracheal tube resistance (ETTr) from airway resistance (Awr) in the equation: Br=Awr−ETTr.

In step 114, the endotracheal tube resistance (ETTr) and the bronchial resistance (Br) are compared to determine if a change in each of these resistances has occurred over time. If the endotracheal tube resistance (ETTr) has increased, at 116, then it is determined at step 120 that the endotracheal tube 74 has become obstructed with mucus buildup or a plug of mucus. After it has been determined that the endotracheal tube 74 is obstructed in step 120, a signal may be sent to the display 56 to indicate to a clinician that the endotracheal tube 74 is obstructed. Upon viewing this indication, the clinician may operate the ventilator to perform an endotracheal tube suction procedure at step 122. The ETT suction procedure may alternatively be initiated by the CPU 58 of the ventilator controller 52. The ETT suction procedure removes the mucus from the endotracheal tube, thus clearing the endotracheal tube for proper delivery of the medical gas to the patient's lungs 44. After the suction has been performed in step 122, the ventilator may return to providing ventilation to the patient at step 100.

At step 114, if the neither the endotracheal tube resistance (ETTr) or the bronchial resistance (Br) have changed, then there are no obstructions and the ventilator is in a normal operating condition, as indicated in step 126. The ventilator continues to operate in providing ventilation to the patient at step 100.

If at step 114 it is determined that the bronchial resistance (Br) has increased, step 118, the increase is indicative that the bronchial tree of the lungs has become obstructed. The lung obstruction as indicated by the increased value of bronchial resistance (Br) may be due to a buildup of mucus and/or other fluid within the lungs 44 of the patient. Fluid or mucus buildup may be treated by performing a lung suctioning procedure. Alternatively, the increased Br may be indicative of a lung disease such as COPD. Therefore, the present invention may help assist a clinician in making a diagnosis of the patient's condition. If it has been identified that the lungs have become obstructed in step 128, a signal may be sent to the display 56 to indicate to a clinician that the lungs are obstructed. Upon viewing this indication, the clinician may perform a lung suction procedure at step 130 to remove the obstruction from the patient's lungs 44. After the lung suction procedure has been performed by a clinician, or automatically by the ventilator, standard ventilation of the patient may be resumed at step 100.

While the present invention has been described in relation to the supply and control of a pressure of medical gas from the ventilator 14, it is understood that an embodiment of the present invention controls the flow of medical gas supplied by the ventilator 14 as the medical gas pressure and flow waveforms supplied by the ventilator 14 are inherently dependent upon each other.

A still further embodiment of the present invention uses other measured or derived values describing the endotracheal tube 74 or the patient's airway to create a more sophisticated ETTr model taking into not only the resistive properties of the endotracheal tube 74 but also the capacitive properties to produce a lumped model. Additionally, in an embodiment of the present invention, ETTr may be modeled using a distributed model such as a transmission line representing multiple resistive and compliance properties of the endotracheal tube.

The present invention provides an advantage over current mechanical ventilation systems in that improved ventilation of a patient receiving ventilation via an endotracheal tube is achieved because the present invention provides compensation for the resistance of the endotracheal tube based from measured values rather than relying on an apriori ETTr model. The present invention provides a method to improve ventilation compensation by creating an improved determination of ETTr. Although the endotracheal tube can be modeled as a simple resistance transfer function, it is also contemplated that the endotracheal tube could be modeled as a lumped RC model or a transmission line model while operating within the scope of the present invention. As a result of the continual monitoring of the endotracheal tube resistance, any changes in the endotracheal tube transfer function caused by the buildup of mucus within the endotracheal tube can be addressed as the changes occur. Furthermore, the determination of ETTr based upon direct measurement of the patient's airway pressure and flow rates allows for the precise pressure or flow compensation to be supplied by the ventilator to compensate for the ETTr.

A further advantage of the present invention is that the method of the present invention provides targeting of an obstruction that causes a detected increase in the patient's airway resistance. The improved targeting of the patient airway obstruction improves the treatment of this obstruction by allowing clinicians to select a treatment procedure that is designed for removing obstructions at the targeted location. Lung suctioning procedures can be harmful to a patient when improperly performed, such as when there is no need for the procedure or the procedure is performed too aggressively. By increasing the ability of the ventilator to identify an obstruction and target the obstruction location, the chance that a patient may be subjected to an improper procedure is reduced.

This written description uses examples to disclose the invention, including the best mode, and also to enable any person skilled in the art to make and use the invention. The patentable scope of the invention is defined by the claims and may include other examples that occur to those skilled in the art. Such other examples are intended to be within the scope of the claims if they have structural elements that do not differ from the literal language of the claims, or if they include equivalent structural elements of insubstantial difference from the literal language of the claims.

Various alternatives and embodiments are contemplated as being with in the scope of the following claims, particularly pointing out and distinctly claiming the subject matter regarded as the invention.

We claim:

1. A method for determining the resistance of an endotracheal tube that is connected to a mechanical ventilator operated by a controller to provide respiratory support to a patient, the method comprising the steps of:

receiving with the controller a first pressure from a ventilator end of the endotracheal tube wherein the first pressure is an airway pressure;

measuring a second pressure from a patient end of the endotracheal tube, wherein the second pressure is a bronchial pressure;

receiving with the controller a flow rate into the endotracheal tube;

deriving with the controller an airway resistance from the airway pressure and the flow rate;

deriving with the controller a bronchial resistance from the bronchial pressure and the flow rate;

deriving with the controller an endotracheal tube resistance from the airway pressure, bronchial pressure, and flow rate;

monitoring the airway resistance; and when an increase in airway resistance is detected, further comparing a change in endotracheal tube resistance to a change in the bronchial resistance to determine a location of an airway obstruction;

wherein if the change in endotracheal tube resistance is greater than the change in bronchial resistance, the controller determines that the endotracheal tube is obstructed.

2. The method of claim 1, wherein a change in the endotracheal tube resistance greater than the change in the bronchial resistance is indicative of an obstruction in the endotracheal tube.

3. The method of claim 1, wherein a change in the bronchial resistance greater than the change in the endotracheal tube resistance is indicative of an obstruction in the lungs of the patient.

4. The method of claim 1 further comprising the steps of:
generating a pressure waveform of medical gas with the medical ventilator based in part upon the derived endotracheal tube resistance;
delivering medical gas to the patient through the endotracheal tube;
continuously deriving the endotracheal tube resistance;
monitoring the derived endotracheal tube resistance; and
updating the pressure waveform generated by the ventilator with a newly derived endotracheal tube resistance.

5. The method of claim 4, wherein the pressure waveform is updated before each breathing cycle delivered by the mechanical ventilator.

6. A method of providing airway compensation control to improve the mechanical ventilation of a patient by a mechanical ventilator operated by a controller, the method comprising the steps of:
deriving with the controller a pressure waveform based upon a target airway pressure waveform and an endotracheal tube model;
delivering medical gas with the mechanical ventilator according to the pressure waveform, the medical gas being delivered to the patient through an endotracheal tube having a patient end and a ventilator end;
measuring a first pressure waveform at the patient end of the endotracheal tube;
receiving with the controller a second pressure waveform at the ventilator end of the endotracheal tube;
receiving with the controller a flow rate at the ventilator end of the endotracheal tube;
deriving with the controller an endotracheal tube resistance from the first pressure waveform, second pressure waveform, and flow rate;
compensating with the controller the pressure waveform in relation to the derived endotracheal tube resistance;
delivering medical gas with the mechanical ventilator according to the compensated pressure waveform; and
compensating the pressure waveform with the controller until the measured first pressure waveform matches the target airway pressure waveform.

7. The method of claim 6, wherein the step of compensating the pressure waveform further comprises the step of increasing an initial amplitude of the pressure waveform to compensate for resistive properties of the endotracheal tube.

8. The method of claim 6, wherein the endotracheal tube resistance further comprises a lumped element model utilizing resistances and compliances.

9. The method of claim 6, wherein the endotracheal tube is modeled as a distributed model.

10. The method of claim 6 further comprising the steps of:
deriving a patient airway resistance with the controller;
monitoring the patient airway resistance with the controller;
wherein if an increase in patient airway resistance is detected:
monitoring the endotracheal tube resistance with the controller; and
identifying with the controller that the endotracheal tube is obstructed and a suction procedure should be performed on the endotracheal tube if an increase in the endotracheal tube is detected; and
monitoring a bronchial resistance with the controller; and
identifying with the controller that there is an obstruction in the patient's lungs and a suction procedure should be performed on the patient's lungs if an increase in the bronchial resistance is detected.

11. A ventilator system for the delivery of medical gas to a patient, the system comprising:
a mechanical ventilator operable to provide medical gas according to a ventilation pressure waveform;
an endotracheal tube in fluid communication with the medical ventilator and placed in a trachea of the patient, the endotracheal tube having a ventilator end and a patient end;
a pressure catheter that extends approximately the length of the endotracheal tube and terminates at a location near the patient end of the endotracheal tube;
a pressure monitor in fluid communication with the pressure catheter, and in fluid communication with a conduit connected at the ventilator end of the endotracheal tube, the pressure monitor measures a differential pressure waveform between a first pressure waveform from the pressure catheter and a second pressure waveform from the conduit as a measured endotracheal tube pressure waveform;
a flow meter in fluid communication with the endotracheal tube, the flow meter measures a flow rate of medical gas into the endotracheal tube; and
a controller communicatively connected to the pressure monitor, the flow meter, and the mechanical ventilator, the controller executes computer readable code embodied on a non-transitory computer readable medium that causes the controller to derive the ventilation pressure waveform based upon a received target pressure waveform, provide the ventilation pressure waveform to the mechanical ventilator for delivery of the medical gas, derive an endotracheal tube resistance from the differential pressure waveform from the pressure monitor and the flow rate from the flow meter, and compensate the ventilator pressure waveform in relation to the derived endotracheal tube resistance, wherein the computer readable code further causes the controller to compare the first pressure waveform to the target pressure waveform and to modify the pressure waveform based upon the derived endotracheal tube resistance until the first pressure waveform matches the target pressure waveform.

12. The ventilator system of claim 11, wherein the received target pressure is a target pressure waveform and the first pressure is a continuous pressure waveform.

13. The ventilator system of claim 12, wherein execution of the computer readable code by the controller further causes the controller to derive airway resistance, monitor the airway resistance for increases, and upon detection of an increase in airway resistance derive a change in endotracheal tube resistance and a change in bronchial resistance, and produce an indication of an obstruction at a location comprising a greater change in resistance between the endotracheal tube and the patient's bronchi.

* * * * *